United States Patent [19]

Yuan

[11] Patent Number: 4,806,493
[45] Date of Patent: Feb. 21, 1989

[54] STABILIZERS FOR USE IN SERUM FOLATE ASSAYS

[75] Inventor: Albert Yuan, Glenside, Pa.

[73] Assignee: ICN Micromedic Systems, Inc., Costa Mesa, Calif.

[21] Appl. No.: 99,663

[22] Filed: Sep. 21, 1987

Related U.S. Application Data

[63] Continuation of Ser. No. 591,147, Mar. 19, 1984, abandoned.

[51] Int. Cl.⁴ .................... G01N 33/567; B65D 69/00
[52] U.S. Cl. ...................................... 436/505; 436/808; 436/825; 436/826; 422/61
[58] Field of Search ................................ 436/503–505, 436/808, 825, 826; 422/61

[56] References Cited

U.S. PATENT DOCUMENTS

| | | |
|---|---|---|
| 4,028,465 | 6/1977 | Lewin et al. |
| 4,332,786 | 6/1982 | Cabelli et al. ........................ 436/505 |
| 4,418,151 | 11/1983 | Forand et al. ....................... 436/505 |
| 4,423,154 | 12/1983 | Gutcho et al. ....................... 436/505 |
| 4,426,455 | 1/1984 | Tovey et al. ......................... 436/505 |

FOREIGN PATENT DOCUMENTS

82/03461  10/1982  World Int. Prop. O. .......... 436/505

OTHER PUBLICATIONS

The Merck Index, 9th Edition, Windholtz et al., eds., Merck & Co. Inc., Rahway, N.J., U.S.A., 1976, pp. 1203–1204.

*Primary Examiner*—Christine M. Nucker
*Attorney, Agent, or Firm*—Lyon & Lyon

[57] ABSTRACT

A serum folate assay wherein the serum folate is stabilized with dimercaptosuccinic acid or thioctic acid.

12 Claims, No Drawings

STABILIZERS FOR USE IN SERUM FOLATE ASSAYS

This application is a continuation of application Ser. No. 591,147, filed Mar. 19, 1984, now abandoned.

This invention relates to the assay of serum folate. It particularly relates to improved stabilizers for use in the assay.

Folate is a generic term for many naturally occurring pteroylglutamic acid analogs. These analogs are hydrolyzed before entering the blood stream. The hydrolysis appears to be mediated by the conjugate enzyme, gammaglutamyl carboxpeptidase. The metabolite, $N^5$-Methyltetrahydrofolate ($N^5MTHF$), is the major circulatory and storage form of folic acid, which is ultimately oxidized to the physiologically active formyl derivative.

The folates play a significant role in the synthesis of purines and thymine required for DNA synthesis and participate in a variety of reactions as coenzymes for single carbon moieties transfer. Humans rely completely on diet for their folate requirements. Since body folate stores are not large, folate deficiency can develop rapidly. Measurement of either serum or red cell folate levels provides useful diagnostic information for determining various types of nutritional anemias. A low serum or red cell folate level is a strong indication that the patient has folate deficiency. In addition, measurement of folate is useful for monitoring a patient's response to therapy.

Recent advances in radioassay technology have resulted in the development of folate radioassays. These methods are less time consuming and more reproducible than microbiological assays and are not subject to interference by antibiotics or antimetabolites.

The folate assay described in this invention utilizes a treated tube procedure which allows a rapid and complete separation of bound from free radioactively labeled antigen. Polypropylene assay tubes are treated with specific folate binding protein. During the assay, radioiodinated folate and endogenous folate from a patient sample are incubated in the treated tube. After the incubation period is completed, the bound folate is separated from free folate by aspiration and washing of the assay tube. The amount of folate bound in the assay tube is compared with values obtained from known folate standards. The folate concentration in the patient sample can then be calculated.

Other folate assay procedures based on competitive binding techniques are known. See for example, U.S. Pat. No. 4,028,465 which discloses the use of dithiopolyols.

In accordance with the present invention, there is disclosed an assay for serum folate employing the competitive binding technique in which endogenous serum folate binding proteins are inactivated by heat or alkaline treatment before the competitive binding step in the presence of a buffered solution containing a stabilizer wherein the improvement comprises employing as a stabilizer a compound selected from dimercaptosuccinic acid (DMSA) or thioctic acid.

The amount of stabilizer employed should be from about 0.05% on a weight-to-reaction volume basis to about 0.5% on a weight-to-reaction volume basis. A preferred concentration is in the range of from 0.1 to 0.3% on a weight-to-reaction volume basis.

These stabilizers have an advantage over previously disclosed stabilizers in that they are more effective and have a longer shelf life than the previous stabilizers.

The stabilizers of this invention can be employed with either manual assays or automated assays.

The following is a description of the reagents and materials employed in the assay kit, and flow diagrams and descriptions of the use of the kit in both an automated and a manual assay.

REAGENTS AND MATERIALS

| | |
|---|---|
| Folate Assay Tubes<br>Assay tubes treated with specific folate binding protein. Store at 4° C. | 200 |
| Folate $^{125}$I Tracer Solution<br>$^{125}$I labeled folate is supplied lyophilized in borate-BSA buffer. Store at 4° C. | 1 vial |
| Folate Denaturing Buffer Solution<br>Contains 95 ml of borate phosphate buffer and 0.01% sodium azide. Store at 4° C. | 1 bottle |
| Folate Assay Buffer Solution<br>Contains 0.1 M borate and 0.01% sodium azide. Store at 4° C. | 1 bottle |
| Folate Standards<br>Six concentrations of folate standards (0, 1.0, 2.5, 5.0, 10.0 and 20.0 ng/ml) are supplied lyophilized in protein based borate buffer. Unreconstituted standards should be stored at 4° C. | 6 vials |
| Folate Control Serum I | 1 vial |
| Folate Control Serum II<br>Two control sera are supplied lyophilzed in defibrinated human plasma. Values are given on the vial labels. Unreconstituted control sera should be stored at 4° C. | 1 vial |
| Folate Stabilizing Solution<br>Contains 5 ml of 5% aqueous solution of 2,3 dimercaptosuccinic acid. Keep vial tightly stopped. | 1 vial |

PREPARATION OF REAGENTS

Prepare master Denaturing Buffer solution by mixing 1 vial of Folate Stabilizing Solution and 1 bottle of Folate Denaturing Buffer Solution. Keep bottle tightly capped.

Folate Tracer Solution and Folate Assay Buffer Solution must be combined before use. Pour the folate tracer solution directly into a clean 500 ml Erlenmeyer flask or amber glass dispenser bottle. Wash out the tracer solution vial three times with the assay buffer solution, adding these washes to the flask or bottle. Add remaining assay buffer solution and mix thoroughly. Place diluted folate tracer solution label provided in the securetainer on the flask or bottle to identify lot number and expiration date of the contents. Insure that sufficient diluted tracer solution is in the dispenser for the present assay. At the end of the assay, store excess diluted tracer solution at 4° C. in an amber bottle or Erlenmeyer flask.

All of the components must be at room temperature before beginning an assay.

STABILITY AND STORAGE

The reagents are stable for a minimum of eight weeks when stored at 4° C. in a dry, dark area. Prolonged exposure to light or heat should be avoided. All reagents should be discarded at their expiration date.

The stability of reconstituted components depends greatly upon the purity of distilled water used and upon the cleanliness of glassware.

RADIOIMMUNOASSAY PROCEDURE

Generaal

Before proceeding with assays, bring all reagents and assay tubes to room temperature. All determinations should be performed in duplicate. A standard curve must be performed with each series of unknowns.

AUTOMATED ASSAY PROCEDURE

Denaturation of Standards, Control Sera, and Patient Samples

Add 250 ul of standard, control or patient sample and 750 ul of Master Folate Denaturing Buffer Solution to a glass minisample tube. Gently vortex. Place minisample tubes into either a heat block with holes for 8×50 mm tubes or a water bath adjusted to 90°–95° C. for 20 minutes. Cool to room temperature before use. Then proceed to next step.

1. For duplicate mode of operation, prepare sample tubes as follows:

| Sample Tube Number | Vial | Contents |
|---|---|---|
| 1 | 1 | Standard: 0 ng/ml |
| 2 | 2 | Standard: 1.0 ng/ml |
| 3 | 3 | Standard: 2.5 ng/ml |
| 4 | 4 | Standard: 5.0 ng/ml |
| 5 | 5 | Standard: 10 ng/ml |
| 6 | 6 | Standard: 20 ng/ml |
| 7 | CI | Control Serum, I |
| 8 | CII | Control Serum, II |
| 9 | | Control Serum |
| 10–100 | | Patient Samples |

2. Check that the water reservoirs are full, the waste containers are empty, and the rinse pumps are primed.
3. Set pipette volumes as follows:

| Pump Name | Volume | Size | Setting |
|---|---|---|---|
| Reagent | 600 ul | 1 ml | 60% |
| Sample | 400 ul | 1 ml | 40% |
| Sample Air | 15 ul | 50 ul | 30% |
| Excess | 30 ul | 200 ul | 15% |
| Rinse | 1.42 | 5 ml | 28.5% |
| Rinse | 1.42 | 5 ml | 28.5% |

4. Clear the reagent transfer tip.
5. Install a tracer dispenser, cycle tip down, prime with 0.75 ml of reagent, cycle tip up and let stand for 5 minutes. Cycle tip down again and prime with an additional 0.5 ml of reagent. Cycle tip to home position.
6. Load Assay racks.
7. Load Sample racks. (If water bath is used for denaturation, be sure the outside of sample tubes are dry before transferring to dry rack).
8. Verify that the ratio of Sample Racks to Assay Racks is appropriate.
9. Set incubation time to 90.0 minutes.
10. Check that incubation temperature is 37° C.
11. Count radioactivity for recommended time.
12. Report results.

AUTOMATED ASSAY FLOW CHART 250 ul of standards, controls patient samples
↓
750 ul Master Denaturing Buffer Solution
↓
Vortex
↓
Heat 20 minutes at 90–95° C.
↓
Cool to room temperature wipe tube dry and vortex
↓
Transfer tube to Dry racks
↓
Load equipment
↓
400 ul of denaturated Standards, Controls and Patient Samples
↓
600 ul Diluted Folate Tracer Solution
↓
Vortex
↓
Incubate 90.0 minutes at 37° C.
↓
Aspirate, then Wash and Aspirate, twice with distilled water
↓
Count for Recommended Time
↓
Report Results

MANUAL ASSAY PROCEDURE

Denaturing (Same as in automated procedure)
Assay

1. Label an appropriate number of folate assay tubes according to the following general outline.

| Sample Tube | Assay Tube | Vial | Contents |
|---|---|---|---|
| 1 | 1,2 | 1 | Standard: 0 ng/ml |
| 2 | 3,4 | 2 | Standard: 1.0 ng/ml |
| 3 | 5,6 | 3 | Standard: 2.5 ng/ml |
| 4 | 7,8 | 4 | Standard: 5.0 ng/ml |
| 5 | 9,10 | 5 | Standard: 10 ng/ml |
| 6 | 11,12 | 6 | Standard: 20 ng/ml |
| 7 | 13,14 | CI | Control I |
| 8 | 15,16 | CII | Control II |
| 9 | 17,18 | | Control Serum |
| 10-100 | 19-200 | | Patient Samples |

2. Transfer 400 ul of the denatured standards, controls and patient samples to the appropriate assay tubes.

3. Add 600 ul of diluted tracer to all assay tubes. Gently vortex.

4. Incubate at 37° C. for 90 minutes.

5. Aspirate liquid from each assay tube. (Note: Be sure that aspirating tip touches the bottom of the assay tube to remove all of the liquid. Avoid scraping inside walls. Use a suitable water aspirator with an Erlenmeyer flask to trap the tube contents.)

6. Wash with 1.3 to 1.5 ml of distilled water twice, aspirating after each wash.

7. Count radioactivity in the tubes on a gamma counter set for the detection of $I^{125}$. Assay tubes may need to be placed in larger tubes compatible with the gamma counter.

MANUAL ASSAY FLOW CHART 250 ul of standards, controls and patient samples
↓
750 ul Master Denaturing Buffer Solution
↓
Vortex
↓
Heat 20 minutes at 90–95° C.
↓
Cool to room temperature and Vortex
↓
400 ul of Denaturated Standards, Controls and patient Samples
↓
600 ul Diluted Folate Tracer Solution
↓
Vortex
↓
Incubate 90.0 minutes at 37° C.
↓
Aspirate, then wash and aspirate, twice, with distilled water
↓
Count for Recommended Time
↓
Report Results The following examples illustrate this invention; however, those skilled in the art realize that many changes and modifications can be made without exceeding the scope of this invention.

EXAMPLE 1

$N^5MTHF$ is spiked into the following protein bases; normal human serum pool, pregnant female serum pool and stripped human serum pool. The average recovery follows:

| ng/ml added | No. of Determinations | Added $N^5MTHF$ Recovered ± 1SD* | % added Recovery |
|---|---|---|---|
| +5 | 6 | 5.73 ± 0.77 | 114.57 |
| +10 | 6 | 10.65 ± 0.88 | 106.48 |
| +15 | 6 | 14.45 ± 2.08 | 96.34 |

EXAMPLE 2

Folic acid is spiked into the normal human serum pools. The average recovery follows:

| Folic acid (ng/ml) | No. of Determinations | Added folic acid Recovered ± 1SD | % added Recovery |
|---|---|---|---|
| +4 | 6 | 4.62 ± 0.58 | 110.2 |
| +8 | 6 | 8.77 ± 0.45 | 107.0 |
| +16 | 6 | 15.92 ± 0.32 | 98.2 |

EXAMPLE 3

Precision data was generated for a low, medium and high folate human serum pool. Five (5) assays using ten (10) samples per pool per assay were tested. Results were calculated by Rodbard calculations.

| | Low pool | Medium pool | High pool |
|---|---|---|---|
| Mean (ng/ml) | 2.26 | 7.00 | 15.93 |
| Intra assay coefficient variation (CV) | 4.75% | 4.07% | 3.08% |
| Inter Assay CV | 5.81% | 5.44% | 6.05% |

EXAMPLE 4

Similar data was obtained by replacing DMSA with dl thioctic Acid.

EXAMPLE 5

0.5% DMSA (weight to volume) was added to the protein based folic acid standards and controls. The stability array results show that the DMSA added standard and controls are stable after 10 weeks storage at 4° C.±2° C. in liquid form.

What is claimed is:

1. In a kit useful in assaying for the presence of serum folate in a sample, said kit including
   in an appropriate container, a serum folate tracer material capable of being combined with said sample,
   in an appropriate container, a serum folate stabilizer capable of being combined with said sample,
   said kit being adapted to utilize a chemical or heat treatment means for inactivating endogenous serum folate binding protein in an inactivation reaction,
   a means for chemically binding a portion of said serum folate and serum folate tracer, and
   the improvement comprising said serum folate stabilizer being selected from the group consisting of dimercaptosuccinic acid and thioctic acid.

2. The kit of claim 1 further comprising, in an appropriate container, a buffer material suitable to buffer said serum folate sample to a pH of from about 7.0 to about 10.0.

3. The kit of claim 1 further comprising, in an appropriate container, alkaline treatment matrial for inactivating endogenous serum folate binding protein in an alkaline treatment reaction.

4. The kit of claim 1 wherein the concentration of said serum folate stabilizer upon combination with said sample during said inactivation reaction is at least about 0.05% on a weight-to-reaction volume basis.

5. The kit of claim 4 wherein the concentration of said serum folate stabilizer upon combination with said sample during said inactivation reaction is from about 0.05 to about 0.4% on a weight-to-reaction volume basis.

6. In a method for assaying for the presence of serum folate in a sample, said method including the steps of
   performing an inactivation reaction on said sample to inactivate endogenous serum folate binding protein, wherein a serum folate stabilizer is present during the inactivation reaction,
   combining a measured amount of the sample with a measured amount of serum folate tracer material to form a combined serum folate material,
   binding a portion of the combined measured sample and measured serum folate tracer material to a specific binder for serum folate,
   separating the bound portion of the combined serum folate and serum folate tracer material from the unbound portion of the combined serum folate and serum folate tracer material, and
   measuring the presence of serum folate tracer in at least one of the bound or unbound portions of the combined serum folate and serum folate tracer material,
   the improvement comprising using a serum folate stabilizer in the combined serum folate material selected from the group consisting of dimercaptosuccinic acid and thioctic acid.

7. The method of claim 6 comprising the further improvement of inactivating endogenous serum folate binding protein using a heating or alkaline treatment inactivation reaction.

8. The method of claim 6 wherein said serum folate stabilizer is in a solution buffered to a pH of from about 7.0 to about 10.0 during said inactivation reaction period.

9. The method of claim 8 wherein said serum folate stabilizer is present in a concentration of at least about 0.05% on a weight-to-volume basis during said inactivation reaction.

10. The method of claim 9 wherein said serum folate stabilizer is present in a concentration of from about 0.05 to about 0.4% on a weight-to-volume basis during said inactivation reaction.

11. A serum folate standard reagent kit for use in standardization of an assay for serum folate, said standard reagent kit comprising
    in an appropriate container, a measured portion of folate, and
    in an appropriate container, a serum folate stabilizer selected from the group consisting of dimercaptosuccinic acid and thioctic acid.

12. A serum folate control reagent kit for use in providing a control in an assay for serum folate, said control reagent kit comprising
    in an appropriate container, a measured portion of a serum containing serum folate, and
    in an appropriate container, a serum folate stabilizer selected from the group consisting of dimercaptosuccinic acid and thioctic acid.

* * * * *